US00PP26176P3

(12) United States Plant Patent
Bacon

(10) Patent No.: US PP26,176 P3
(45) Date of Patent: Dec. 1, 2015

(54) APRICOT TREE NAMED 'SUAPRITHIRTEEN'

(50) Latin Name: *Prunus armeniaca*
Varietal Denomination: Suaprithirteen

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 133 days.

(21) Appl. No.: 13/998,546

(22) Filed: Nov. 7, 2013

(65) Prior Publication Data
US 2015/0128316 P1 May 7, 2015

(51) Int. Cl.
*A01H 5/08* (2006.01)

(52) U.S. Cl.
USPC ..... Plt./186

(58) Field of Classification Search
USPC ..... Plt./186
See application file for complete search history.

*Primary Examiner* — Keith O. Robinson
(74) *Attorney, Agent, or Firm* — Knobbe, Martens, Olson & Bear, LLP

(57) ABSTRACT

A new and distinct apricot tree, *Prunus armeniaca* cv. 'Suaprithirteen' is characterized by having large fruit, a later harvest time and fewer incidences of split and shattered stones.

1 Drawing Sheet

Latin name of the genus and species claimed: *Prunus armeniaca.*

Variety denomination: 'Suaprithirteen'.

BACKGROUND AND SUMMARY OF THE INVENTION

The present invention relates to a new and distinct variety of apricot tree, herein after referred to by the cultivar name 'Suaprithirteen'. The new variety was first originated by hybridized in May 2008 by Terry A. Bacon as breeder number: 'AP933'.

The new variety is characterized by having large fruit, later harvest time and fewer incidences of split and shattered stones.

The seed parent is 'Suaprinine' (U.S. Plant Pat. No. 16,507), and the pollen parent is unknown, being from a bulk of 8 pollen parents. The parent varieties were first crossed in February 2005, with the date of first sowing being February 2006, and the date of first flowering being February 2008. The new apricot variety 'Suaprithirteen' was first asexually propagated by Terry Bacon near Wasco, Kern County, Calif. in January 2009 by grafting.

The new variety 'Suaprithirteen' can be distinguished from its seed parent, 'Suaprinine' (U.S. Plant Pat. No. 16,507) in that harvest of fruit from the new variety 'Suaprithirteen' starts May 12, five days later than 'Suaprinine' (U.S. Plant Pat. No. 16,507). The fruit of the new variety 'Suaprithirteen' also has a larger diameter at 58 mm compared to 54 mm of 'Suaprinine' (U.S. Plant Pat. No. 16,507).

The new variety 'Suaprithirteen' ripens about the same time as 'Suapriseven' (U.S. Plant Pat. No. 10,165) but the new variety has fewer incidences of split and shattered stones along with a larger fruit diameter at 58 mm compared to 54 mm of 'Suapriseven' (U.S. Plant Pat. No. 10,165).

The new variety 'Suaprithirteen' has been shown to maintain its distinguishing characteristics through successive asexual propagations by, for example, grafting.

The new variety 'Suaprithirteen' has the same seed parent, 'Suaprinine' (U.S. Plant Pat. No. 16,507), as 'Suaprieleven' (U.S. Ser. No. 13/998,508), and the pollen parent comes from the same bulk of 8 pollen parents. 'Suaprieleven' and 'Suaprithirteen' differ from each other in bloom date, harvest date and fruit weight. The new variety 'Suaprithirteen' has a bloom date of February 24 while 'Suaprieleven' has a bloom date of February 12. 'Suaprithirteen' has a harvest date of May 12 compared to April 28 for 'Suaprieleven'. The new variety 'Suaprithirteen' has a fruit weight of 96 grams while 'Suaprieleven' has a fruit weight of 65 grams.

BRIEF DESCRIPTION OF THE PHOTOGRAPH

The accompanying color photographic illustration shows typical specimens of the foliage and fruit of the present new apricot variety 'Suaprithirteen'. The illustration shows the upper and lower surface of the leaves, a view of the fruit as a whole, and a sectional view of a fruit divided across its suture plane to show flesh color, pit cavity and the stone remaining in place in a 3 year old plant.

The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to 3 year old 'Suaprithirteen' plants grown in the vicinity of Wasco, Kern County, Calif., during 2013 and is believed to apply to plants of the variety grown under similar conditions of soil and climate elsewhere.

TREE

General: (Measurements taken on 3 year old tree unless otherwise noted).

*Tree size*.—Medium. Normal for most apricot varieties. Reaches a height of 3.5 meters with normal pruning.

*Spread*.—3 meters.

*Tree vigor*.—Medium. Growth of approximately 1.8 to approximately 2 meters height the first growing season.

*Tree growth*.—Semi-upright spreading.

*Tree productivity*.—Productive.

*Tree form*.—Vase formed.

*Bearer*.—Regular.

*Fertility*.—Unknown.

*Branching*.—Medium.

*Tree canopy density*.—Medium. Pruning is required to open tree vase shape, allowing more sunlight to center of tree.

*Tree hardiness*.—Hardy in all fruit growing areas of California. Winter chilling requirement is approximately 600 hours at or below 7.2° C.

*Tree disease resistance/susceptibility*.—No specific testing for relative plant disease resistance/susceptibility has been undertaken. Under close observation in the area of Wasco, Kern County, Calif., no particular plant/fruit disease resistance/susceptibility has been observed.

Trunk: (Measurements at 30 cm above soil line).

*Trunk diameter*.—Approximately 21 cm.

*Trunk texture*.—Smooth to slightly shaggy.

*Trunk color*.—About Medium Greyed-Green 197D in exposed areas to Dark Greyed-Orange 166A in recesses, becoming darker with age.

Branches: (Measurements at approximately 90 cm above soil line).

*Branch diameter*.—Approximately 9 cm.

*Branch texture*.—Smooth on 1$^{st}$ year wood, increasing roughness with tree age.

*Branch color*.—Branches vary from about Medium Greyed-Green 197D to Medium Greyed-Green 197B in exposed areas and Medium Greyed-Orange 165B in recesses.

*Branch lenticels*.—Few. Size: Medium. Density (no./cm$^2$): Variable, about 5. Color: About Dark Greyed-White 156A. Typical size: Approximately 4 mm in length and approximately 2 mm wide.

Flowering shoots: (Data taken in July at midpoint of current-season growth. Color and sizes described may vary due to differences in sunlight, vigor and temperatures.).

*Flowering shoot size*.—Average diameter: approximately 8 mm.

*Flowering shoot color*.—Topside: About Dark Greyed-Orange 176A. Underside: About Dark Greyed-Orange 176A.

*Flowering shoot lenticels*.—Size: Medium, about 10/cm2. Color: About Dark Greyed-White 156A. Diameter: Approximately 0.5 mm.

*Flowering shoot leaf buds*.—Shape: Ovoid. Width: Approximately 1.5 mm. Length: Approximately 2 mm. Color: About Dark Greyed-Orange 165A. Texture: Smooth.

*Flowering shoot flower buds*.—Shape: Elongated ovoid. Width: Approximately 1.5 mm. Length: Approximately 4 mm. Color: About Dark Greyed-Orange 165A. Number: Usually 2. Texture: Smooth.

*Internode length*.—Medium and variable, approximately 1-4 cm midway on flowering shoots. Width: About 6 mm. Texture: Smooth. Density of Buds: Medium. Distribution: Generally isolated on spurs and one year old shoots and older wood. Ration of Wood (leaf) Bud to Flowering Shoots: 1/2.

Root:

*Habit*.—Branching.

*Color*.—About White 155A.

*Time it takes to initiate roots*.—10 days.

*Time it takes to produce a rooted plant*.—6 weeks.

FOLIAGE

Leaves: (Data taken in July on fully expanded leaf at midpoint of current-season growth. Color and sizes described may vary due to differences in sunlight, vigor and temperatures).

*Leaf size*.—Medium. Length: Medium, approximately 6 cm. Width: Medium, approximately 6 cm.

*Leaf thickness*.—Medium.

*Leaf color*.—Upper surface: About Dark Green 136A. Lower surface: About Medium Green 138A.

*Leaf form*.—Circular.

*Leaf tip*.—Cuspidate.

*Leaf base*.—U-shaped.

*Leaf margin*.—Crenate.

*Venation*.—Pinately net veined.

*Vein color*.—About Medium Green 138B.

*Leaf surface texture*.—Smooth.

*Leaf blade (ratio length/width)*.—Small.

*Shape in cross section*.—Flat.

*Angle at apex*.—Medium.

*Profile*.—Flat.

*Leaf blade tip*.—Curved downwardly.

*Angle of tip*.—Acute.

*Undulation of margin*.—Slight.

Petiole:

*Length*.—Medium, approximately 18 mm.

*Diameter*.—Approximately 1 mm.

*Color*.—About Medium Green 138B, becoming Medium Greyed-Red 181A in sunlight.

*Texture*.—Smooth.

Stipules:

*Number/leaf bud*.—Approximately 0 to 2.

*Typical length*.—Approximately 3 mm.

*Color*.—About Medium Green 139C.

*Persistence*.—Fall off.

*Texture*.—Smooth.

Glands:

*Form*.—Globose.

*Number*.—Approximately 0 to 3.

*Position*.—On petiole, alternate.

*Size*.—Medium, approximately 0.6 mm.

*Color*.—About Dark Greyed-Orange 165A.

FLOWERS

General:
*First bloom*.—February 24, in Wasco, Calif.
*Location of first bloom*.—Upper portion of the canopy.
*Full bloom*.—February 28, in Wasco, Calif.
*Location of full bloom*.—Middle of the canopy.
*Time of bloom*.—From approximately February 24-February 28.
*Duration of bloom*.—Medium, about 10 days.
*Diameter of fully open flower*.—Medium, approximately 27 mm.
*Flower aroma*.—Very slight.
*Shape*.—Rosaceous.

Peduncle:
*Length*.—Medium, approximately 3 mm.
*Diameter*.—Medium, approximately 2 mm.
*Color*.—About Light Yellow-Green 145C, with highlights of about Medium Red 46D.
*Pubescence*.—Absent.

Petals:
*Number*.—5.
*Arrangement*.—Overlapping.
*Length*.—Approximately 12 mm.
*Diameter*.—Approximately 10 mm.
*Shape*.—Circular.
*Apex shape*.—Rounded.
*Base shape*.—Narrows at point of attachment.
*Color*.—Inner Surface: About Light Red 36D. Outer Surface: About Light Red 36D.
*Surface texture*.—Smooth (upper and lower surface).
*Margins*.—Smooth and slightly undulating.
*Frequency of flowers with double petals*.—None.
*Margin waviness*.—Weak.
*Base angle*.—Wide.
*Pubescence of inner surface*.—Absent.
*Pubescence of outer surface*.—Absent.

Sepals:
*Number*.—5.
*Length*.—Approximately 6 mm.
*Diameter*.—Approximately 4.5 mm.
*Shape*.—Broad ovate.
*Color*.—About Medium Red 42B.
*Surface texture*.—Smooth (inner and outer surface).
*Margins*.—Smooth, entire.
*Positioning*.—Adpressed to petals.
*Pubescence of inner surface*.—Absent.
*Pubescence of outer surface*.—Absent.
*Frequency of flowers with double sepals*.—None.

Stamens:
*Number*.—Approximately 19.
*Length*.—Approximately 10 mm.
*Filament color*.—About White 155A.
*Anther color*.—About Medium Yellow 14C.
*Pollen color*.—About Medium Yellow 14C.
*Position*.—Perigynous.
*Amount of pollen*.—Medium.

Pistil:
*Number*.—Usually one.
*Average length*.—Approximately 8 mm.
*Ovary diameter*.—Approximately 3 mm.
*Pubescence*.—Medium.
*Stigma extension in comparison to anthers*.—Below with anthers.
*Frequency of supplementary pistils*.—Few.

Receptacle:
*Depth*.—Medium, approximately 4 mm.
*Pubescence of inner surface* (*at pink bud stage*).—Absent.
*Pubescence of outer surface*.—Absent.

FRUIT (Data taken at firm-ripe on mature tree managed to obtain maximum quality under conditions stated in Description of Variety. Timing, colors and sizes described may vary due to differences in sunlight, vigor and temperatures).

General:
*Fruit harvest*.—Date of First Pick: Approximately May 12, in Wasco, Calif. Date of Last Pick: Approximately May 21, in Wasco, Calif.
*Date of description*.—Approximately May 15.
*Maturity when described*.—Firm.
*Season ripening*.—Medium.
*Position of maximum diameter*.—Towards the middle.
*Symmetry about the suture*.—Nearly symmetrical.

Fruit size:
*Length* (*stem end to apex*).—Approximately 58 mm.
*Diameter in line with suture plane*.—Approximately 58 mm.
*Diameter perpendicular to suture plane*.—Approximately 54 mm.
*Average weight*.—Approximately 96 gm.

Fruit form:
*Viewed from apex*.—Round, nearly symmetric.
*Viewed from side, facing suture*.—Rounded, nearly symmetric.
*Viewed from side, perpendicular to suture*.—Round-elongated, nearly asymmetric.

Fruit apex shape: Rounded, slightly indented at tip.

Fruit stem cavity:
*Shape*.—Rounded.
*Depth*.—Medium, approximately 1 cm.
*Breadth*.—Approximately 1.5 cm.

Fruit stem:
*Length*.—Medium, Approximately 8 mm.
*Diameter*.—Approximately 2 mm.
*Color*.—About Medium Green 143C.
*Adherence to stone*.—Medium.
*Texture*.—Smooth.

Fruit skin:
*Thickness*.—Medium.
*Adherence to flesh*.—Medium.
*Surface texture*.—Smooth.
*Pubescence*.—Moderate to scant, short, does not need roll up when rubbed.
*Bloom*.—Slight.
*Ground color*.—About Medium Orange-Red 31B.
*Overcolor*.—About Medium Orange-Red 34A.
*Taste*.—Neutral.
*Reticulation*.—Slight.
*Tendency to crack*.—Slight, in wet season.

Fruit flesh:
*Ripens*.—Evenly.
*Texture*.—Melting.
*Fibers*.—Few.
*Flavor*.—Sweet-mild.
*Brix*.—Approximately 15°.
*Juice*.—Moderate.
*Aroma*.—Slight.

*Color*.—About Medium Orange-Red 31C.
*Anthocyanin color under skin*.—Absent.
*Anthocyanin color of flesh*.—Absent.
*Anthocyanin color around stone*.—Absent.
*Acidity*.—Low, 1.2%.
*Eating quality*.—Good.
*Stone/flesh ratio*.—4 g/96 g.
*Firmness*.—Medium.

Pit cavity size:
*Length*.—Approximately 26 mm.
*Diameter in line with suture plane*.—Approximately 26 mm.
*Diameter perpendicular to suture plane*.—Approximately 11 mm.
*Color*.—About Medium Orange-Red 31A.

Fruit use: Fresh market.

Fruit shipping/keeping quality: Medium.

Stone:
*Stone freeness*.—Cling, over entire surface.
*Degree of adherence to flesh*.—Medium.
*Size*.—Medium.
*Size compared to fruit*.—Small.
*Length*.—Medium, approximately 26 mm.
*Suture*.—Slightly sunken.
*Diameter in line with suture plane*.—Approximately 22 mm.
*Diameter perpendicular to suture plane*.—Approximately 11 mm.
*Angle of stalk end*.—Obtuse.
*Stone form* (*viewed from side*).—Round-elongated.
*Stone form* (*viewed from stem end*).—Oval, narrow.
*Stone form* (*viewed from ventral end*).—Flattened.
*Stone base shape*.—Rounded.
*Stone apex shape*.—Nearly rounded.
*Hilum*.—Narrow.
*Stone surface*.—Slightly pitted with a few ridges extending the length.
*Stone halves*.—Nearly equal.
*Stone ridges*.—Continuous.
*Stone outgrowing keel*.—Partly developed.
*Stone tendency to split*.—Rare.
*Stone color*.—About Medium Grey-Brown 199D.
*Position of maximum*.—Middle.
*Sides*.—Nearly equal.
*Pits*.—Shallow, irregular.
*Fibers*.—Retains short fiber-like threads along the ridges.
*Ventrical edge*.—Thin with slight wing towards middle.
*Dorsal edge*.—Medium, continuous.

What is claimed is:

1. A new and distinct variety of apricot tree named 'Suaprithirteen' as herein illustrated and described.

* * * * *

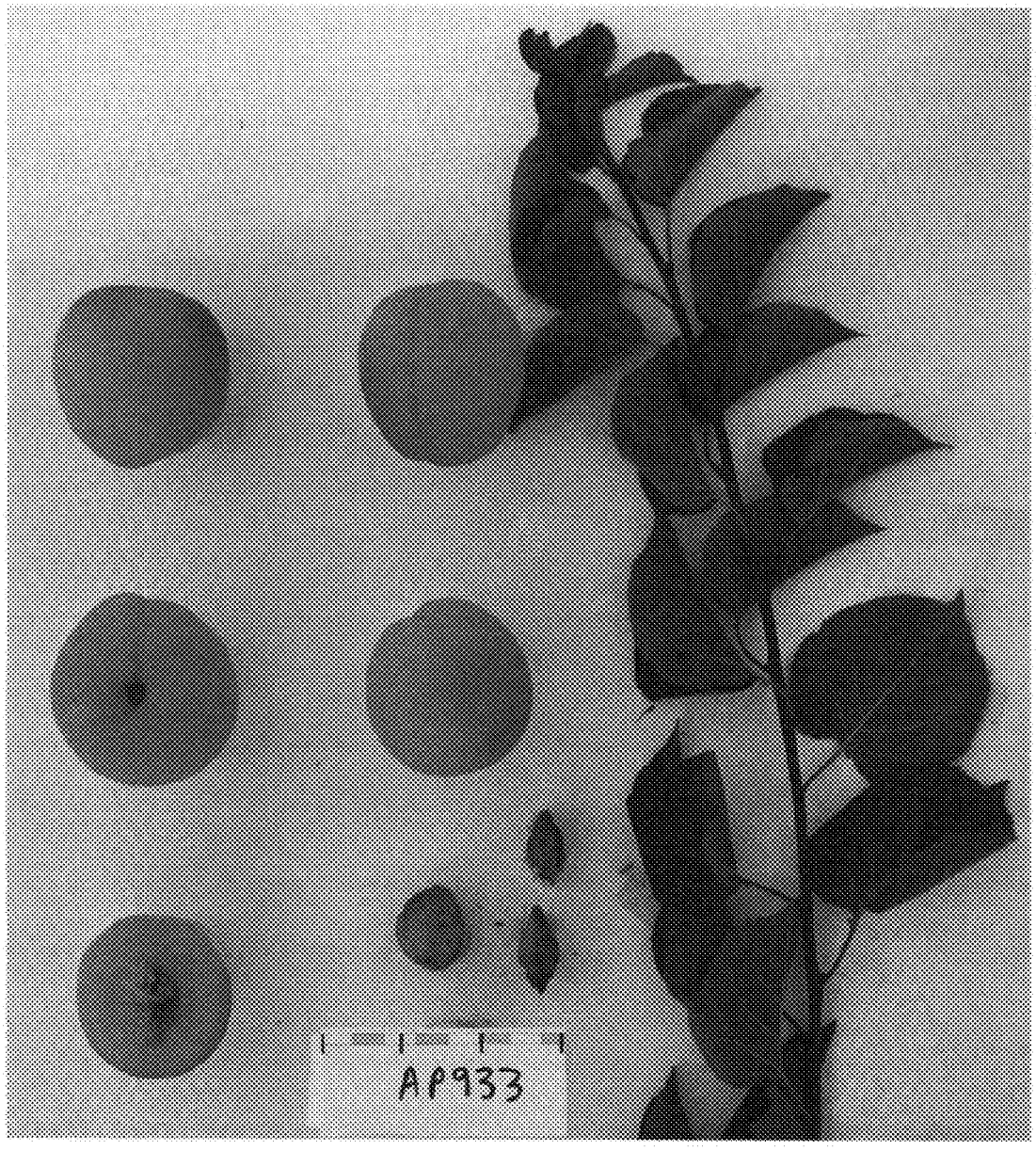
AP933